United States Patent
Hansen

(10) Patent No.: US 6,537,980 B1
(45) Date of Patent: Mar. 25, 2003

(54) VITAMIN D ANALOGUES AND THEIR PHARMACEUTICAL USE

(75) Inventor: Kai Holst Hansen, Herlev (DK)

(73) Assignee: Leo Pharmaceutical Products Ltd., Ballerup (DK)

(*) Notice: Subject to any disclaimer, the term of this patent is extended or adjusted under 35 U.S.C. 154(b) by 0 days.

(21) Appl. No.: 09/959,306

(22) PCT Filed: Apr. 12, 2000

(86) PCT No.: PCT/DK00/00177

§ 371 (c)(1),
(2), (4) Date: Oct. 23, 2001

(87) PCT Pub. No.: WO00/64869

PCT Pub. Date: Nov. 2, 2000

Related U.S. Application Data

(60) Provisional application No. 60/130,638, filed on Apr. 23, 1999.

(30) Foreign Application Priority Data

Apr. 23, 1999 (GB) .............................................. 9909442

(51) Int. Cl.[7] ...................... A61K 31/593; C07C 401/00
(52) U.S. Cl. ........................................ 514/167; 552/653
(58) Field of Search ........................... 552/653; 514/167

(56) References Cited

U.S. PATENT DOCUMENTS

| | | | |
|---|---|---|---|
| 5,411,949 A | 5/1995 | Neef et al. .................. | 514/167 |
| 6,017,908 A * | 1/2000 | Reddy ......................... | 514/167 |

FOREIGN PATENT DOCUMENTS

WO      WO 91/15475      10/1991

OTHER PUBLICATIONS

Database STN [On line] Grue–Soerensen G et al: "Chemistry and biology of 23–oxa–aro–and 23 thia–aro–Vitamin D analogs with high antiproliferative and low calcemic activity" retrieved from STN International, File Caplus, accession No. 1995:706058 Database accession No. 123:160073 XP002901167 abstract & Proc. Workshop Vitamin.D, 1994, pp. 75–66, 9th (Vitamin D) issn: 0721–7110.

* cited by examiner

*Primary Examiner*—Sabiha Qazi
(74) *Attorney, Agent, or Firm*—Birch, Stewart, Kolasch & Birch, LLP

(57) ABSTRACT

The present invention relates to compounds of general formula (I) wherein $R^1$ and $R^2$, which may be the same or different, represent $(C_1–C_4)$alkyl, and $R^3$ represents hydrogen, halogen, $(C_1–C_4)$alkyl, or $O—(C_1–C_4)$alkyl, and in-vivo hydrolysable esters there with pharmaceutically acceptable acids. The present compounds are of value in the human and veterinary practice.

15 Claims, No Drawings

VITAMIN D ANALOGUES AND THEIR PHARMACEUTICAL USE

This application is the National Phase of International Application PCT/DK00/00177 filed Apr. 12, 2000 which designated the U.S. and that International Application was published under PCT Article 21(2) in English and claims the benefit of provisional application No. 60/130,638 filed Apr. 23, 1999.

This invention relates to hitherto unknown vitamin D compounds which shows strong activity in inducing differentiation and inhibiting undesirable proliferation of certain cells, including skin cells and cancer cells, as well as anti-inflammatory and immunomodulating effects, to pharmaceutical preparations containing these compounds, to dosage units of such preparations, and to their use in the treatment and prophylaxis of diseases characterised by abnormal cell differentiation and/or cell proliferation such as cancer, leukemia, myelofibrosis, and psoriasis, of a number of disease states including hyperparathyroidism, particularly secondary hyperparathyroidism associated with renal failure, diabetes mellitus, hypertension, acne, alopecia, skin ageing, AIDS, neurodegenerative disorders such as Alzheimer's disease, host versus graft reactions, rejection of transplants, inflammatory diseases such as rheumatoid arthritis and asthma, for prevention and/or treatment of steroid induced skin atrophy, and for promoting osteogenesis and treating osteoporosis.

It has been shown that $1\alpha,25$-dihydroxy-vitamin $D_3$ ($1,25(OH)_2D_3$) influences the effects and/or production of interleukins (Muller, K. et al., *Immunol. Lett.*, 17, 361–366 (1988)), indicating the potential use of this compound in the treatment of diseases characterised by a dysfunction of the immune system, e.g. autoimmune diseases, AIDS, host versus graft reactions, and rejection of transplants or other conditions characterised by an abnormal interleukin-1 production, e.g. inflammatory diseases such as rheumatoid arthritis and asthma.

It has also been shown that $1,25(OH)_2D_3$ is able to stimulate the differentiation of cells and inhibit excessive cell proliferation (Abe, E. et al., *Proc. Natl. Acad. Sci., U.S.A.*, 78, 4990–4994 (1981)), and it has been suggested that this compound might be useful in the treatment of diseases characterised by abnormal cell proliferation and/or cell differentiation such as leukemia, myelofibrosis and psoriasis.

Also, the use of $1,25(OH)_2D_3$, or its pro-drug $1\alpha$-OH—$D_3$, for the treatment of hypertension (Lind, L. et al., *Acta Med. Scand.*, 222, 423–427 (1987)) and diabetes mellitus (Inomata, S. et al., *Bone Mineral.*, 1, 187–192 (1986)) has been suggested. Another indication for $1,25(OH)_2D_3$ is suggested by the recent observation of an association between hereditary vitamin D resistance and alopecia: treatment with $1,25(OH)_2D_3$ may promote hair growth (Editorial, Lancet, March 4, p. 478 (1989)). Also, the fact that topical application of $1,25(OH)_2D_3$ reduces the size of sebaceous glands in the ears of male Syrian hamsters suggests that this compound might be useful for the treatment of acne (Malloy V. L. et al., The Tricontinental Meeting for Investigative Dermatology, Washington, (1989)).

However, the therapeutic possibilities in such indications are severely limited by the well-known potent effect of $1,25(OH)_2D_3$ on calcium metabolism; elevated blood concentrations will rapidly give rise to hypercalcemia. Thus, this compound and some of its potent synthetic analogues are not satisfactory for use as drugs in the treatment of e.g. psoriasis, leukemia or immune diseases which may require continuous administration of the drug in relatively high doses.

A number of vitamin D analogues have recently been described that show some degree of selectivity in favour of the cell differentiation inducing/cell proliferation inhibiting activity in vitro as compared with the effects on calcium metabolism in vivo (as measured in increased serum calcium concentration and/or increased urinary calcium excretion), which adversely limit the dosage that can safely be administered. One of the first of these to appear, calcipotriol (INN) or calcipotriene (USAN), has been developed on the basis of this selectivity and is now recognised world-wide as an effective and safe drug for the topical treatment of psoriasis.

A study with another vitamin D analogue, Seocalcitol [1(S),3(R)-dihydroxy20(R)-(5'-ethyl-5'-hydroxy-hepta-1'(E), 3'(E)-diene-1'-yl)-9,10-secopregna-5(Z),7(E),10(19)-triene], selected on this basis supports the concept that systemically administered vitamin D analogues may inhibit breast cancer cell proliferation in vivo at sub-toxic doses (Colston, K. W. et al., *Biochem. Pharmacol.* 44, 2273–2280 (1992) and Mathiasen, I. S. et al., *J. Steroid Biochem. Molec. Biol.*, 46, 365–371 (1993)).

There is a continuing need for new vitamin D analogues with an acceptable combination of desired therapeutic activity and minimum toxic effects. Compounds having a structure similar to the compounds of the present invention are disclosed in EP 522 013. However, said compounds exhibit considerable skin irritation, and are therefore less suitable for topic administration or local treatment of skin diseases.

The compounds of the present invention provide hitherto undisclosed vitamin D analogues with immunosuppressive and cell proliferation inhibitory activities without the undesired side effects of increased serum calcium levels and skin irritation.

The present invention relates to compounds of the general formula I

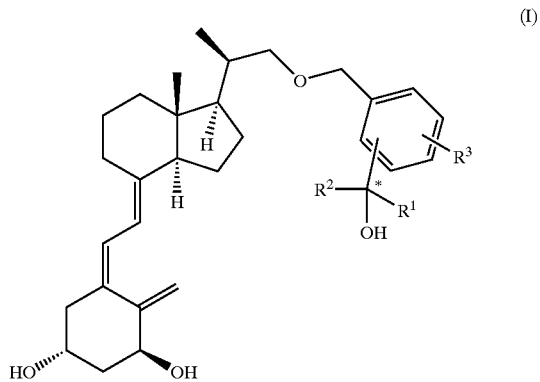

wherein $R^1$ and $R^2$, which may be the same or different, represent $(C_1-C_4)$alkyl, and $R^3$ represents hydrogen, halogen, $(C_1-C_4)$alkyl, or $O$—$(C_1-C_4)$alkyl, and in-vivo hydrolysable esters thereof with pharmaceutically acceptable acids.

The configuration at the tentative chiral carbon atom (starred in formula I and Ia (below)) may be R or S. In preferred compounds of the invention the starred carbon atom is substituted with identical alkyl groups ($R^1=R^2$) and is thus achiral.

More particularly, the invention relates to compounds of the general formula Ia:

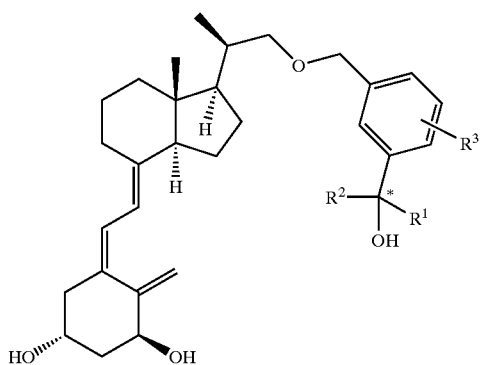

(Ia)

wherein $R^1$, $R^2$, and $R^3$ have the meanings defined above.

Preferred are compounds of formula Ia wherein $R^1$ and $R^2$ independently represent methyl or ethyl and wherein $R^3$ represents hydrogen, F, Cl, methyl, ethyl, or methoxy. Furthermore, preferred compounds of formula Ia are compounds wherein the group $R^3$ is in the 4-position or in the 5-position. Further preferred compounds of formula Ia are compounds wherein $R^1$ and $R^2$ both represent methyl and $R^3$ represents hydrogen, F, or methyl. Most preferred compounds of formula Ia are compounds wherein $R^3$ represents hydrogen, 5-methyl, or 4-fluoro, and $R^1$ and $R^2$ both represent methyl.

The invention also includes diastereoisomers of the compounds of formula I in pure form or as a mixture of such diastereoisomers.

Specifically preferred compounds of the invention are selected from the group consisting of:

1(S),3(R)-Dihydroxy-20(R)-[((3-(2-hydroxy-2-propyl)-phenyl)-methoxy)-methyl]-9,10-secopregna-5(Z),7(E),10(19)-triene;

1(S),3(R)-Dihydroxy-20(R)-[((3-(2-hydroxy-2-propyl)-5-methyl-phenyl)-methoxy)-methyl]-9,10-secopregna-5(Z),7(E),10(19)-triene;

1(S),3(R)-Dihydroxy-20(R)-[((3-(2-hydroxy-2-propyl)-5-methoxy-phenyl)-methoxy)-methyl]-9,10-secopregna-5(Z),7(E),10(19)-triene;

1(S),3(R)-Dihydroxy-20(R)-[((3-(2-hydroxy-2-propyl)-4-fluoro-phenyl)-methoxy)-methyl]-9,10-seco-pregna-5(Z),7(E),10(19)-triene, and in-vivo hydrolysable esters thereof with pharmaceutically acceptable acids.

The term "Alkyl" as used herein refers to any univalent group derived from an alkane by removal of a hydrogen atom from any carbon atom, and includes the subclasses of normal alkyl (n-alkyl), and primary, secondary and tertiary alkyl groups respectively, and having the number of carbon atoms specified, including for example ($C_1$–$C_4$)alkyl, e.g. methyl, ethyl, n-propyl, and isobutyl. Alkane refers to an acyclic branched or unbranched hydrocarbon having the general formula $C_nH_{2n+2}$, and therefore consisting entirely of hydrogen atoms and saturated carbon atoms.

The compounds of formula Ia may conveniently be prepared from the vitamin D derivative 1 described in Tetrahedron 43 4609 (1987) by the route outlined in Scheme I. The corresponding ortho and para substituted analogues of formula I may be prepared in a similar way.

1 is reduced, e.g. with $NaBH_4$, to the alcohol 2, which may be transformed to the compounds of formula III in two ways. compound 2 is either alkylated with a side chain building block A—C($R_1$)($R_2$)—$C_6H_3$($R_3$)—$CH_2$—Z (A is a suitable, protected hydroxy group, e.g. tetrahydropyranyloxy or trialkylsilyloxy; Z is a leaving group, such as Cl, Br, I, or tosyl; and $C_6H_3$($R_3$) is o-phenylene, m-phenylene or p-phenylene, or the hydroxy group in compound 2 is transformed to a leaving group, e.g. by tosylation to form compound 11, and then converted to III by treatment under basic conditions with a side chain building block of formula A—C($R_1$)($R_2$)—$C_6H_3$($R_3$)—$CH_2OH$.

The conversion of III to Ia involves a photoisomerisation step and a deprotection step, analogous to the steps used in last stages of the synthesis of other vitamin D analogues, cf. EP patent No. 0 227 826.

The side chain building blocks of formula A—C($R_1$)($R_2$)—$C_6H_3$($R_3$)—$CH_2$—Z are either known compounds or may be prepared as described in PCT/DK90/00323. The side chain building blocks of formula A—C($R_1$)($R_2$)—$C_6H_3$($R_3$)—$CH_2OH$ are either known compounds or may be prepared from A—C($R_1$)($R_2$)—$C_6H_3$($R_3$)—$CH_2$—Z by simple aqueous hydrolysis.

Scheme 1

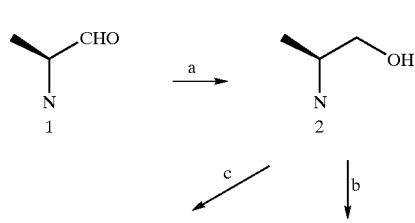

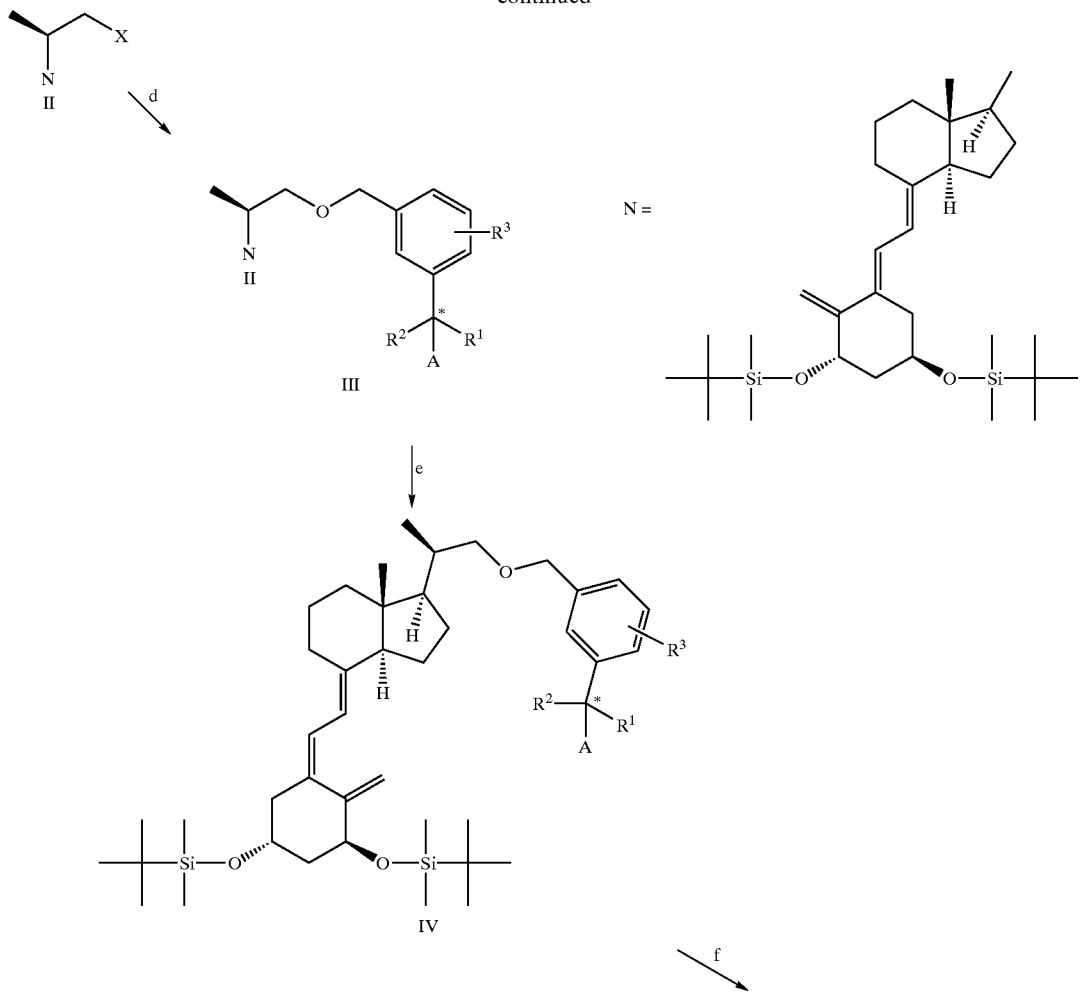

Notes to the reaction scheme:
a) Reduction, e.g. with NaBH$_4$.
b) Alkylation with the side chain fragment
   A—C(R$_1$)(R$_2$)—C$_6$H$_3$(R$_3$)—CH$_2$—Z
   in the presence of a base, e.g. KOH, KOBu$^t$, or KH, with or without a catalyst, e.g. 18-crown-6, in a dry solvent, e.g. THF.
c) Conversion of OH to leaving group X, e.g. by tosylation for X = O—Ts.
d) Reaction with the side chain building block
   A—C(R$_1$)(R$_2$)—C$_6$H$_3$(R$_3$)—CH$_2$OH
   in the presence of a base, e.g. NaH, in a solvent such as DMF.
e) Isomerisation with hv in the presence of a triplet sensitizer, e.g. anthracene.
f) Deprotection with TBAF or HF.

The following standard abbreviations are used throughout this disclosure:
Bu$^t$=tert-butyl, DMF=N,N-dimethylformamide, Et=ethyl, Ether=diethyl ether, Me=methyl,
PPTS=pyridinium p-toluenesulfonate, Py=pyridine, TBAF=tetra-n-butylammonium fluoride,
TBS=tert-butyldimethylsilyl, THF=tetrahydrofuran, THP=tetrahydro-4H-pyran-2-yl, Ts=tosyl.
TES=triethylsilyl.

Pharmacological Methods

In order to demonstrate the effectiveness of the compounds of formula I, comparative data are presented in Table A below. The column headings: "HaCaT, rel.", "Calc., rel.", "Receptor binding rel.", and "Skin irritation score" are explained in the following.

An assay for the rating of test compounds for antiproliferative activity in skin cells, e.g. antipsoriatic effect, is the in vitro assay using HaCaT, a spontaneously immortalised, non-tumorigenic human skin keratinocyte cell line (Mørk Hansen, C. et al., J. Invest. Dermatol 1, 44–48 (1996)), measuring $^3$H -thymidine uptake. In Table A, column "HaCaT, rel.", the antiproliferative activity in skin cells of compound 100 of Example 1 herein(relative to 1,25(OH)$_2$ D$_3$, Calcitriol) is listed; as mentioned, compound 100 exhibit antiproliferative activity in skin cells of the same potency as the compound Calcitriol of the prior art.

Generally, the classical effects of 1,25(OH)$_2$D$_3$ on the calcium balance in the organism, including calcemic and calciuric activities, are unwanted in the vitamin D analogues of the present invention, in which selectivity for e.g. inhibition of the proliferation of certain cells, absence of calcemic effects and skin irritation is desired. Thus, the calcemic activity of the compounds was determined in rats in vivo, as previously described (Binderup, L., Bramm, E., *Biochem. Pharmacol.* 37, 889–895 (1988)). In Table A, column "Calc., rel.", the calcemic activities of compound 100 of Example 1 herein (relative to 1,25(OH)$_2$D$_3$) is listed; as mentioned, compound 100 of the present invention does exhibit very low calcemic activity compared to the compounds Calcitriol and compound No. 111 of EP 522 013 of the prior art.

Furthermore, the binding to the vitamin D receptor relative to the binding of Calcitriol of the present compounds compared to compounds of the prior art was determined in vitro as previously described (Binderup, L., Bramm, E., *Biochem. Pharmacol.* 37, 889–895 (1988)).

Skin irritation was assessed in hairless guinea pigs. Randomised occlusive patch testing for 48 hours was used. Each analogue was tested at three dose levels (500 µg/ml, 50 µg/ml, and 5 µg/ml) and a placebo solution was also included. Assessment of skin irritation was blinded and based upon clinical grading and objective measurement of cutaneous blood flow (laser Doppler perfusion imaging, LDPI) and erythema (Minolta ChromaMeter). Furthermore, epidermal thickness as an indication of epidermal hyperplasia was measured.

The irritancy scores were as defined below:

0 Substances of no irritation

+ Substances of doubtful or very low irritancy compared to calcitriol

++ Substances of low irritancy compared to calcitriol

+++ Substances with irritances in the same range as calcitriol

++++ Substances of more irritancy than calcitriol

+++++ Very irritative substances compared to calcftriol

It appears from Table A that the Compound 100 exhibits considerably less skin irritation than compounds of the prior art, while the potency in the HaCaT-assay (psoriasis model) is similar to that of 1,25(OH)$_2$D$_3$ and the calcemic activity is negligible and comparable to that of compound no. 111 of EP522013.

TABLE A

Biological Tests of Compound 100 and Reference Compounds

| Compound | Skin irritation score | Receptor binding rel., ¤ | HaCaT rel., ¤ | Calc. rel.** |
|---|---|---|---|---|
| Calcipotriol | +++ | 0.5 | 2 | 0.005 |
| Calcitriol | +++ | 1 | 1 | 1 |
| 100, Ex. 1 | + | 0.01 | 1 | 0.001 |
| Ref. | ++++ | 0.5 | 40 | 0.07 |

Notes to Table A
**The values are relative to 1,25(OH)$_2$D$_3$; a value greater than 1 indicates a compound which is more active than 1,25(CH)$_2$D$_3$in the assay.
¤Calculated as the ratio between the IC$_{50\ value}$ of 1,25(OH)$_2$D$_3$ and the IC$_{50}$ value of the compound, the IC$_{50}$ being the concentration which results in 50% inhibition of the $^3$H-thymidine incorporation compared to controls.
Ref. Reference compound (compound 111 of EP 522013)

Structurally, the compounds of formula I herein are closely related to the compounds of formula I disclosed in EP 522 013. However, the present compounds show surprisingly less skin irritation than the compounds of EP 522 013. In order to demonstrate this surprising effect, the compound No. 100 of Example 1 herein has been compared to the compound No. 111 of EP 522 013. The only structural difference between said compounds is the chain length between the oxygen linked to carbon No. 22 and the phenyl ring, where said oxygen is directly linked to the phenyl ring in compound 111 of EP 522 013. compared to said oxygen being linked to the phenyl ring in the present compound 100 via a methylene group.

The present compounds are intended for use in pharmaceutical compositions which are useful in the local or systemic treatment of human and veterinary disorders as described above.

The present compounds may be used in combination with other pharmaceuticals or treatment modalities. In the treatment of psoriasis the present compounds may be used in combination with e.g. steroids or with other treatments e.g. light- or UV-light-treatment or the combined PUVA-treatment. In the treatment of cancer the present compounds may be used in combination with other anti-cancer drugs or anti-cancer treatments, such as radiation treatment. In the prevention of graft rejection and graft versus host reaction, or in the treatment of auto-immune diseases, the present compounds may advantageously be used in combination with other immunosuppressive or immunoregulating drugs or treatments, e.g. with cyclosporin A.

The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis or eye diseases topical or enteral forms are preferred.

While it is possible for an active ingredient to be administered alone as the raw chemical, it is preferable to present it as a pharmaceutical formulation. Conveniently, the active ingredient comprises from 0.1 ppm to 0.1% by weight of the formulation.

The formulations, both for veterinary and for human medical use, of the present invention thus comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include e.g. those in a form suitable for oral, ophthalmic, rectal, parenteral (including subcutaneous, intramuscular and intravenous), transdermal, intra-articular and topical, nasal or buccal administration.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

Formulations for rectal administration may be in the form of a suppository incorporating the active ingredient and a carrier, or in the form of an enema.

Formulations suitable for parenteral administration conveniently comprise a sterile oily or aqueous preparation of the active ingredient which is preferably isotonic with the blood of the recipient. Transdermal formulations may be in the form of a plaster or a patch.

Formulations suitable for intra-articular or ophthalmic administration may be in the form of a sterile aqueous preparation of the active ingredient which may be in microcrystalline form, e.g. in the form of an aqueous microcrystalline suspension. Liposomal formulations or biodegradable polymer systems may also be used to present the active ingredient for both intra-articular and ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops.

Formulations suitable for administration to the nose or buccal cavity include powder, self-propelling and spray formulations, such as aerosols and atomizers.

In addition to the aforementioned ingredients, the formulations of this invention may include one or more additional ingredients, such as diluents, binders, preservatives etc.

The compositions may further contain other therapeutically active compounds usually applied in the treatment of the above mentioned pathological conditions, such as other immunosuppressants in the treatment of immunological diseases, or steroids in the treatment of dermatological diseases.

The present invention further concerns a method for treating patients suffering from one of the above pathological conditions, said method consisting of administering to a patient in need of treatment an effective amount of one or more compounds of formula I, alone or in combination with one or more excipients or other therapeutically active compounds usually applied in the treatment of said pathological conditions. The treatment with the present compounds and/or with further therapeutically active compounds may be simultaneous or with intervals.

In the systemic treatment daily doses of from 0.001–2 µg per kilogram bodyweight, preferably from 0.002–0.3 µg/kg of mammal bodyweight, for example 0.003–0.3 µg/kg of a compound of formula I are administered, typically corresponding to a daily dose for an adult human of from 0.2 to 25 µg. In the topical treatment of dermatological disorders, ointments, creams or lotions containing from 0.1–1000 µg/g, and preferably from 1–500 µg/g, and more preferably from 10–250 µg/g, of a compound of formula I are administered. For topical use in ophthalmology ointments, drops or gels containing from 0.1–1000 µg/g, and preferably from 1–500 µg/g, more preferably from 10–250 µg/g, of a compound of formula I are administered. The oral composition s are formulated, preferably as tablets, capsules, or drops, containing from 0.05–100 µg, preferably from 0.1–50 µg, of a compound of formula I, per dosage unit.

The invention will now be further described in the following General Procedures, Preparations and Examples:

GENERAL PROCEDURES, PREPARATION AND EXAMPLES

General

The exemplified compounds of formula I are listed in Table 2, whereas intermediates of preparations 1 to 8 are listed in Table 1.

For nuclear magnetic resonance spectra (300 MHz) chemical shift values (δ) are quoted for deuteriochloroform solutions relative to internal tetramethylsilane (δ=0) or chloroform (δ=7.25). The value for a multiplet, either defined (doublet (d), triplet (t), quartet (q)) or not (m) at the approximate mid point is given unless a range is quoted (s=singlet, b=broad). Coupling constants (j) are given in Hertz (Hz), and are sometimes approximated to the nearest unit.

Ether is diethyl ether, and was dried over sodium. THF was dried over sodium-benzophenone. Petroleum ether refers to the pentane fraction. Reactions were routinely run under an argon atmosphere at room temperature unless otherwise noted. The work-up procedure referred to involves dilution with the specified solvent (otherwise the organic reaction solvent), extraction with water and then brine, drying over anhydrous $MGSO_4$ and concentration in vacuo to give a residue.

Chromatography was performed on silica gel.

TABLE 1

Preparations of Compounds of Formulas III and IV

| Compound No. | Preparation No. | Formula Scheme 1 | $R^1$ | $R^2$ | $R^3$ | A |
|---|---|---|---|---|---|---|
| 4 | 3 | III | Me | Me | H | O—THP |
| 5 | 4 | IV | Me | Me | H | O—THP |
| 6 | 5 | III | Me | Me | 5-Me | O—THP |
| 7 | 6 | IV | Me | Me | 5-Me | O—THP |
| 8 | 7 | III | Me | Me | 5-OMe | O—THP |
| 9 | 8 | IV | Me | Me | 5-OMe | O—THP |
| 10 | 10 | III | Me | Me | H | O—TES |
| 11 | 11 | IV | Me | Me | H | O—TES |

TABLE 2

Exemplified Compounds of formula Ia

| Compound No. | Example No. | $R^1$ | $R^2$ | $R^3$ |
|---|---|---|---|---|
| 100 | 1 | Me | Me | H |
| 101 | 2 | Me | Me | 5-Me |
| 102 | 3 | Me | Me | 5-OMe |
| 100 | 4 | Me | Me | H |
| 103 | | Et | Et | H |
| 104 | | Et | Et | 5-Me |
| 105 | | Me | Me | 4-F |

General Procedures

General Procedure 1: Preparation of a Compound of Formula III by Alkylation of Compound 2

To a solution of compound 2 (862 mg, 1.5 mmol) in dry tetrahydrofuran (10 ml) potassium hydride (1.0 ml 20% suspension in oil) and a side chain building block of formula A—C(R$_1$)(R$_2$) C$_6$H$_3$(R$_3$)—CH$_2$—Z (6,75 mmol) were added, and the reaction mixture stirred vigorously. 18-crown-6 (650 mg, 5.8 mmol) was dissolved in dry tetrahydrofuran (5 ml) and added dropwise over 20 minutes. After a further 90 minutes stirring, water (40 ml) was carefully added to the reaction mixture. After the reaction had subsided, the reaction mixture was diluted with ether (100 ml) and the organic phase consecutively extracted with water (3×50 ml) and aqueous saturated sodium chloride (50 ml). After drying and removal of the solvent in vacuo, the product was purified by chromatography (silica gel, 10% ether in petroleum ether as eluant) to give the desired compound as a colourless oil.

General Procedure 2: Isomerisation of a Compound of Formula III to the Corresponding 5(Z) Isomer IV A solution of a compound of formula III (1 mmol), anthracene (800 mg, 4.5 mmol) and triethylamine (1 drop) in dichloromethane (60 ml) under argon in a Pyrex flask was irradiated with light from a high pressure ultraviolet lamp, type TQ 718-Z2 (Hanau) at room temperature for 35 minutes. The solution was filtered and concentrated in vacuo. The residue was purified by chromatography (silica gel, 10% ether in petroleum ether as eluant) to give the desired compound as a colourless oil.

General Procedure 3: Deprotection of a Compound of Formula IV to the Corresponding Compound of Formula I A compound of formula IV (1 mmol) was dissolved in ethyl acetate (1.0 ml). Acetonitrile (25 ml) was added under vigorous stirring. A solution of 5% hydrofluoric acid in acetonitrile/water 8:1 (12 ml) was added and the reaction mixture stirred under argon at room temperature for 45 minutes. Ethyl acetate (150 ml) was added, and the reaction mixture consecutively extracted with saturated aqueous sodium hydrogen carbonate (60 ml), water (3×60 ml) and saturated aqueous sodium chloride (50 ml) dried with magnesium sulphate and concentrated in vacuo. The residue was purified by chromatography (silica gel, 20% pentane in ethyl acetate as eluant) to give the title compound.

Preparations

Preparation 1: 1(S),3(R)-bis-tert-Butyldimethyl-silyloxy-20 (R)-hydroxymethyl-9,10-secopregna-5(E),7(E) 10(19)-triene (Compound 2)

A stirred, ice-cooled solution of the aldehyde 1 (5 g) in THF (20 ml) and ethanol (70 ml) was treated with sodium borohydride (0.35 g). After 10 minutes the reaction mixture was partitioned between ethylacetate and water, and the organic layer was washed with brine and dried. Concentration in vacuo gave the title compound. $^1$H NMR: δ=0.05 (bs, 12H), 0.56 (s, 3H), 0.86 (s, 9H), 0.89 (s, 9H), 0.96 (d, 3H, J=7), 1.1–2.1 (m, 15H), 2.31 (bd, 1H), 2.55 (dd, 1H, J=14 and 5), 2.86 (bd, 1H), 3.48 (dd, 1H, J=10 and 7), 3.71 (dd, 1H, J=11 and 4), 4.21 (m, 1H), 4.52 (m, 1H), 4.93 (bs, 1H), 4.98 (bs, 1H), 5.82 (d, 1H, J=11.5), and 6.44 (d, 1H, J=11.5).

Preparation 3: 1(S),3(R)-bis-tert-Butyldimethyl-silyloxy-20 (R)-D-toluenesulphonyloxy-methyl-9,10-secopregna-5(E),7 (E),10(19)-triene (Compound 3)

Compound 2 (5 g) was dissolved in dichloromethane (25 ml) and pyridine (3 ml), and the solution was stirred and ice-cooled during the addition of p-toluenesulphonyl chloride (2.5 g). The reaction mixture was allowed to stand at 5° C. overnight before being partitioned between ethyl acetate and water. The organic layer was washed consecutively with saturated cupric sulphate solution (twice), water, 5% sodium hydrogen carbonate solution, and brine, and then dried and concentrated in vacuo. The residue was purified by chromatography (200 g silica gel; 5% ether in petroleum ether as etuant) to give the title compound, (m.p. 98–100° C. from MeOH), $^1$H NMR: δ=0.035 (s, 3H), 0.044 (s, 3H), 0.051 (s, 3H), 0.056 (s, 3H), 0.45 (s, 3H), 0.85 (s, 9H), 0.88 (s, 9H), 0.89 (d, 3H, J=6), 1.15–2.05 (m, 14H), 2.28 (bd, 1H), 2.44 (s, 3H), 2.52 (dd, 1H, J=14 and 5), 2.84 (bd, 1H), 3.81 (m, 1H), 4.11 (m, 1H), 4.20 (m, 1H), 4.51 (m, 1H), 4.93 (bs, 1H), 4.97 (bs, 1H), 5.97 (d, 1H, J=11), 6.42 (d, 1H, J=11), 7.33 (bd, 2H), 7.78 (bd, 2H).

Preparation 3: Compound 4

Method: General Procedure 1

Starting material: 2-(2-(3-bromomethylphenyl)-2-propyloxy)-tetrahydro-4H-pyran $^1$H NMR δ=7.42(s,1H), 7.3(m,3H), 6.44(d,1H), 5.61(d,1H), 4.98(s,1H), 4.93(s,1H), 4.51(dd,1H), 4.46(s,2H), 4.42(m,1H), 4.21(m,1H), 3.93(m, 1H), 3.54(dd,1H), 3.39(m,1H), 3.27(t,1H), 2.85(d,1H), 2.54 (dd,1H), 2.30(d,1H), 2.01(t,1H), 1.95–1.30(m,19H), 1.66(s, 3H), 1.50(s,3H), 0.98(d,3H), 0.91(s,9H), 0.89(s,9H), 0.53(s, 3H), 0.06(s,12H).

Preparation 4: Compound 5

Method: General Procedure 2

Starting material: Compound 4 $^{13}$C NMR δ=148.1, 147.0, 140.6, 138.4, 134.9, 127.8, 125.9, 125.9, 124.8, 124.8, 124.7, 122.9, 117.8, 111.0, 95.2, 77.7, 74.5, 72.8, 71.8, 67.3, 63.2, 56.0, 53.2, 45.8, 45.4, 44.6, 39.7, 36.0, 32.0, 31.9, 28.6, 26.7, 26.3, 25.7, 25.6, 25.2, 23.2, 21.8, 20.5, 18.0, 17.9, 17.1,12.2, −4.9−, −5.0, −5.3

Preparation 5: Compound 6

Method: General Procedure 1

Starting material: 2-(2-(3-bromomethyl-5-methylphenyl)-2-propyloxy)-tetrahydro-4H-pyran $^1$H NMR δ=7.21(s,1H), 7.15(s,1H), 7.05(s,1H), 6.44(d,1H), 5.81(d,1H), 4.98(s,1H), 4.94(s,1H), 4.54(dd,1H), 4.43(s,2H), 4.40(m,1H), 4.21(m, 1H), 3.95(m,1H), 3.54(dd,1H), 3.35(m,1H), 0.25(t,1H), 2.86 (d,1H), 2.34(s,3H), 2.30(d,1H), 2.0(t,1H), 1.95–1.20(m, 19H), 1.65,(s,3H), 1.48(s,3H), 0.98(d,3H), 0.90(s,9H), 0.85 (s,9H), 0.53(s,3H), 0.05(s,12H).

Preparation 6: Compound 7

Method: General Procedure 2

Starting material: Compound 6 $^1$H NMR δ=7.21(s,1H), 7.15(s,1H), 6.90(s,1H), 6.22(d,1H), 6.00(d,1H), 5.17(s,1H), 4.85(s,1H), 4.4–4.3(m,4H), 4.18(m,1H), 3.95(m,1H), 3.53 (dd,1H), 3.35(m,1H), 3.24(t,1H), 2.78(d,1H), 2.41 (d,1H), 2.34(s,3H), 2.21 (dd,1H), 1.95(t,1H), 1.9–1.25(m,19H), 1.65 (s,3H), 1.48(s,3H), 0.99(d,3H), 0.90(s,18H), 0.25(s,3H), 0.07(s,12H).

Preparation 7: Compound 8

Method: General Procedure 1

Starting material: 2-(2-(3-bromomethyl-5-methoxyphenyl)-2-propyloxy)-tetrahydro-4H-pyran $^1$H NMR δ=6.98(s,1H), 6.92(d,1H), 6.79(s,1H), 6.44(d,1H), 5.83(d,1H), 4.98(s,1H), 4.93(s,1H), 4.5(dd,1H), 4.45(m, 3H), 4.21 (m,1H), 3.95(m,1H), 3.80(s,3H), 3.55(dd,1H), 3.40(m,1H), 3.26(t,1H), 2.87(d,1H), 2.56(dd,1H), 2.32(d, 1H), 2.01 (t,1H), 1.95–1.40(m,19H), 1.64(s,3H), 1.48(s,3H), 1.00(d,3H), 0.93(s,9H), 0.85(s,9H), 0.53(s,3H), 0.05(s, 12H).

Preparation 8: Compound 9

Method: General Procedure 2

Starting material: Compound 8 $^1$H NMR δ=6.98(s,1H), 6.91 (s,1H), 6.82(s,1H), 6.21 (d,1H), 6.00(d,1H), 5.17(s, 1H), 4.58(s,1H), 4.46(s,2H), 4.40(m,1H), 4.35(m,1H), 4.17 (m,1H), 3.95(m,1H), 3.80(s,3H), 3.55(dd,1H), 3.38(m,1H), 3.25(t,1H), 2.80(d,1H), 2.42(dd,1H), 2.2(dd,1H), 1.96(t, 1H), 1.95–1.2(m,19H), 1.64(s,3H), 1.48(s,3H), 0.98(d,3H), 0.88(s,18H), 0.52(s,3H), 0.05(s,12H).

Preparation 9: 2-(3-Bromomethylphenyl)-2-triethylsilyloxy-propan

Imidazole (10.1 g, 148 mmol) was dissolved in dry DMF (100 ml) triethylchlorosilane (15.6 ml, 148 mmol) was added and the reaction stirred under argon at room temperature for 30 minutes. A solution of 2-(3-bromomethylphenyl)-2-propanol (17.0 g, 74 mmol) dissolved in dry DMF (100 ml) was added dropwise over 15 minutes. After stirring for a further 15 minutes ethyl acetate (1100 ml) was added and the mixture consecutively extracted with 1N hydrochloric acid (2×50 ml), water (3×200 ml), and saturated aqueous sodium chloride (200 ml) dried over magnesium sulphate and concentrated in vacuo. The residue was purified by chromatography (silica gel, 1% ether in pentane as eluant) to give the title compound as a colourless oil.

$^1$H NMR δ=7.50 (t,1H), 7.41(dt,1H), 7.29(t,1H), 7.23(dt, 1H), 4.50(s,2H), 1.57(s,6H), 0.95(t,6H), 0.59(q,9H),

Preparation 10 Compound 10

Method: General Procedure 1

Starting material: 2-(3-Bromomethylphenyl)-2-triethylsilyloxy-propan 1H NMR δ=7.43(m,1H), 7.37(m, 1H), 7.27(t,1H), 7.17(m,1H), 6.45(d,1H), 5.82(m,1H), 4.98 (m,1H), 4.94(m,1H), 4.53(dd,1H), 4.48(s,2H), 4.22(m,1H), 3.54(dd,1H), 3.26(dd,1H), 2.86(m,1H), 2.55(dd,1H), 2.32 (m,1H), 2.08–1.20(m,1 4H), 1.56(s,6H), 0.99(d,3H), 0.94(t, 9H), 0.90(s,9H), 0.86(s,9H), 0.58(q,6H), 0.53(s,3H), 0.06 (m,12H)

Preparation 11 Compound 11

Method: General Procedure 2

Starting material: Compound 10 $^1$H NMR δ=7.45–7.10 (m,4H), 6.22(d,1H), 6.01 (d,1H), 5.18(d,1H), 4.86(d,1H), 4.47(s,2H), 4.39(m,1H), 4.18(m,1H), 3.54(dd,1H), 3.25(dd, 1H), 2.81(d,1H), 2.44(dd,1H), 2.21(dd,1H), 2.04–1.15(m, 14H), 1.56(s,6H), 0.98(d,3H), 0.93(t,9H), 0.87(s,18H), 0.58 (q,6H), 0.52(s,3H), 0.06(s,12H), Example 1

1(S),3(R)-Dihydroxy-20(R)-[((3-(2-hydroxy-2-propyl)-phenyl)-methoxy)-methyl]-9,10-seco-pregna-5(Z),7(E),10(19)-triene (Compound 100)

Method: General Procedure 3

Starting material: Compound 5 $^{13}$C NMR δ=149.2, 147.6, 142.9, 138.8, 133.0, 128.2, 126.0, 124.9, 123.6, 123.5, 117.1, 111.8, 74.7, 73.0, 72.5, 70.8, 66.8, 56.2, 53.5, 45.7, 45.3, 42.8, 39.8, 36.1, 31.8, 29.0, 26.8, 23.5, 22.1, 17.3, 12.4

Example 2

1(S),3(R)-Dihydroxy-20(R)-[((3-(2-hydroxy-2-propyl)-5-methyl-phenyl)-methoxy)-methyl]-9,10-seco-pregna-5(Z),7(E),10(19)-triene (Compound 101)

Method: General Procedure 3

Starting material: Compound 7 $^1$H NMR δ=7.24(s,1H), 7.21 (s,1H), 7.04(s,1H), 6.36(d,1H), 6.02(d,2H), 5.32(s,1H), 4.99(s,1H), 4.44(s,2H), 4.39(m,2H), 4.21 (m,1H), 3.55(dd, 1H), 3.24(dd,1H), 2.62(d,1H), 2.58(d,1H), 2.35(s,3H), 2.30–1.20(m,14H), 1.56(s,6H), 0.98(d,3H), 0.54(s,3H).

Example 3

1(S),3(R)-Dihydroxy-20(R)-[((3-(2-hydroxy-2-propyl)-5-methoxy-phenyl)-methoxy)-methyl]-9,10-seco-pregna-5(Z),7(E), 10(19)-triene (Compound 102)

Method: General Procedure 3

Starting material: Compound 9 $^1$H NMR δ=7.01(s,1H), 6.97(s,1H), 6.80(s,1H), 6.36(d,1H), 6.02(d,1H), 5.32(s,1H), 4.99(s,1H), 4.46(s,2H), 4.41m,1H), 4.20(m,1H), 3.81(s,3H), 3.58(dd,1H), 3.25(t,1H), 2.81(dd,1H), 2.57(dd,1H), 2.3(dd, 1H), 2.0–1.3(m,14H), 1.56(s,6H), 0.99(d,3H), 0.54(s,3H).

Example 4

1(S),3(R)-Dihydroxy-20(R)-[((3-(2-hydroxy-2-propyl)-phenyl)-methoxy)-methyl]-9,10-seco-pregna-5(Z),7(E),10(19)-triene (Compound 100)

Method: General Procedure 3

Starting material: Compound 11 $^{13}$CNMR δ=149.2, 147.6, 142.9, 138.8, 133.0, 128.2, 126.0, 124.9, 123.6, 123.5, 117.1, 111.8, 74.7, 73.0, 72.5, 70.8, 66.8, 56.2, 53.5, 45.7, 45.3, 42.8, 39.8, 36.1, 31.8, 29.0, 26.8, 23.5, 22.1, 17.3, 12.4

Example 5

Capsules Containing Compound 100

Compound 100 was dissolved in arachis oil to a final concentration of 1 μg of Compound 111/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100 μl of Compound 111 in oil solution, such that each capsule contained 0.1 μg of Compound 100.

Example 6

Dermatological Cream Containing Compound 100

In 1 g almond oil was dissolved 0.05 mg of Compound 100. To this solution was added 40 g of mineral oil and 20 g of self-emulsifying beeswax. The mixture was heated to liquefy. After the addition of 40 ml hot water, the mixture was mixed well. The resulting cream contains approximately 0.5 μg of Compound 100 per gram of cream.

Example 7

Injectable Solution Containing Compound 100

A solution useful for injections containing

10 μg of compound No. 100 herein 15.4 mg disodium phosphate dihydrate 2 mg sodium dihydrogen phosphate dihydrate 0.8 mg sodium chloride 5 mg sodium ascorbate 5 mg Solutol® HS 15 ad 1 ml water for injection.

I claim:

1. A compound of the formula I

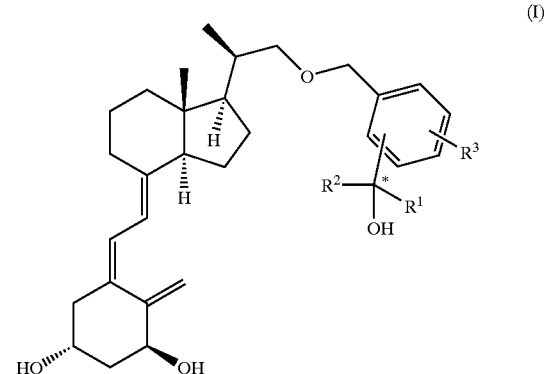

wherein $R^1$ and $R^2$, which may be the same or different, represent $(C_1-C_4)$alkyl, and $R^3$ represents hydrogen, halogen, $(C_1-C_4)$alkyl, or $O-(C_1-C_4)$alkyl, and in-vivo hydrolysable esters thereof with pharmaceutically acceptable acids.

2. A compound according to claim 1 having the formula Ia

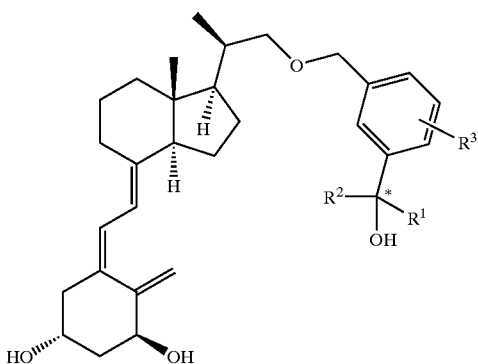

wherein $R^1$ and $R^2$, which may be the same or different, represent $(C_1-C_4)$alkyl, and $R^3$ represents hydrogen, halogen, $(C_1-C_4)$alkyl, or $O-(C_1-C_4)$alkyl, and in-vivo hydrolysable esters thereof with pharmaceutically acceptable acids.

3. The compound according to claim, 1 or 2, wherein $R^1$ presents methyl or ethyl.

4. The compound according to claim 1 or 2, wherein $R^2$ represents methyl or ethyl.

5. The compound according to claim 1 or 2, wherein $R^3$ represents hydrogen, F, Cl, methyl, ethyl, or methoxy.

6. The compound according to claim 1 or 2, wherein $R^3$ is in the 5-position.

7. The compound according to claim 1 or 2, wherein $R^1$ and $R^2$ both represent methyl, and $R^3$ represents hydrogen, F, or methyl.

8. The compound according to claim 1 or 2, wherein $R^3$ represents 5-methyl or 4-flouro.

9. A diastereoisomer of the compound according to claim 1 or 2 in pure form;

or a mixture of diastereoisomers of the compound according to claim 1 or 2.

10. The compound according to claim 1 or 2, which is selected from the group consisting of:

1(S), 3(R)-Dihydroxy-20(R)-[((3-(2-hydroxy-2-propyl)-phenyl)-methoxy)-methyl]-9,10-seco-pregna-5(Z),7(E),10(19)-triene;

1(S),3(R)-Dihydroxy-20(R)-[((3-(2-hydroxy-2-propyl)-5-methyl-phenyl)-methoxy)-methyl]-9,10-seco-pregna-5(Z),7(E),10(19)-triene;

1(S),3(R)-Dihydroxy-20(R)-[((3-(2-hydroxy-2-propyl)-5-methoxy-phenyl)-methoxy)-methyl]-9,10-seco-pregna-5(Z),7(E),10(19)-triene;

1(S),3(R)-Dihydroxy-20(R)-[((3-(2-hydroxy-2-propyl)-4-flurophenyl)-methoxy)-methyl]-9,10-seco-pregna-5(Z),7(E),10(19)-triene;

and in vivo hydrolysable esters thereof with pharmaceutically acceptable salts.

11. A pharmaceutical composition containing an effective amount of the compound.according to claim 1 or 2, together with pharmaceutically acceptable carriers and/or auxiliary agents.

12. A pharmaceutical composition according to claim 11 in dosage unit form.

13. The pharmaceutical composition according to claim 12, wherein said dosage unit comprises from 0.05–100 mg of said effective amount of the compound.

14. A method for the treatment and prophylaxis of psoriasis, said method comprising administration of an effective amount of the composition according to claim 12.

15. The pharmaceutical composition according to claim 12, wherein said dosage unit comprise from 0.1–50 mg of said effective amount of the compound.

* * * * *